(12) United States Patent
Kaganove et al.

(10) Patent No.: US 7,794,699 B2
(45) Date of Patent: Sep. 14, 2010

(54) NANO-STRUCTURED BLOOD SUBSTITUTES

(75) Inventors: Steven N. Kaganove, Midland, MI (US); Paul Satoh, Holt, MI (US); Petar R. Dvornic, Midland, MI (US)

(73) Assignee: Michigan Molecular Institute, Midland, MI (US)

( * ) Notice: Subject to any disclaimer, the term of this patent is extended or adjusted under 35 U.S.C. 154(b) by 446 days.

(21) Appl. No.: 11/324,826

(22) Filed: Jan. 4, 2006

(65) Prior Publication Data

US 2006/0147414 A1 Jul. 6, 2006

Related U.S. Application Data

(60) Provisional application No. 60/641,498, filed on Jan. 5, 2005.

(51) Int. Cl.
*A61K 31/74* (2006.01)
(52) U.S. Cl. .................................... 424/78.17
(58) Field of Classification Search ........................ None
See application file for complete search history.

(56) References Cited

U.S. PATENT DOCUMENTS

| | | | | |
|---|---|---|---|---|
| 5,714,166 | A | * | 2/1998 | Tomalia et al. ............... 424/486 |
| 5,731,095 | A | * | 3/1998 | Milco et al. ................... 428/482 |
| 5,869,538 | A | | 2/1999 | Van Liew et al. |
| 6,127,428 | A | | 10/2000 | Lundgren et al. |
| 6,750,300 | B2 | * | 6/2004 | Mahieu et al. .............. 525/523 |

FOREIGN PATENT DOCUMENTS

| | | |
|---|---|---|
| WO | WO 99/21541 | 5/1999 |
| WO | WO 02/34297 | 5/2002 |
| WO | WO 02077037 A2 * | 10/2002 |

OTHER PUBLICATIONS

Fang et al, Hyperbranched Polyimides for Gas Separation Applications. 1. Synthesis and Characterization, Macromolecules, 2000, 33, 4639-4646.*
Gudipati et al, Hyperbranched Fluoropolymer and Linear Poly(ethylene glycol) Based Amphiphilic Crosslinked Networks as Efficient Antifouling Coatings: An insight in the Surface Compositions, Topographies, and Morphologies, Journal of Polymer Science: Part A: Polymer Chemistry, 2004, 42, 6193-6208.*
http://www.dendrimerweb.com/, accessed Nov. 5, 2009.*

* cited by examiner

*Primary Examiner*—Michael G Hartley
*Assistant Examiner*—Paul Dickinson
(74) *Attorney, Agent, or Firm*—Price, Heneveld, Cooper, DeWitt & Litton, LLP (57) ABSTRACT

An improved synthetic blood substitute which exhibits excellent long-term storage stability at both high and low temperatures is suitable for use in various biomedical and biotechnical applications, including resuscitation of trauma victims that have suffered massive hemorrhaging, and transfusions for human and veterinary surgical procedures. The artificial blood solution comprises an aqueous carrier, and a dendritic polymer that is capable of carrying oxygen dissolved in the aqueous carrier. The dendritic polymer comprises fluorocarbon moieties and hydrophilic moieties.

16 Claims, 10 Drawing Sheets

NANO-STRUCTURED BLOOD SUBSTITUTES

CROSS-REFERENCE TO RELATED APPLICATION

This application claims priority under 35 U.S.C. §119(e) to U.S. Provisional Application No. 60/641,498 entitled NANO-STRUCTURED BLOOD SUBSTITUTES, filed Jan. 5, 2005, by Steven N. Kaganove, Paul Satoh and Petar R. Dvornic, the entire disclosure of which is incorporated herein by reference.

FIELD OF THE INVENTION

This invention relates to compounds that are useful as synthetic oxygen carriers for biomedical and biotechnical applications.

BACKGROUND OF THE INVENTION

Over the past forty years the development of synthetic blood substitutes has attracted increasingly serious interest from the medical community. This once fanciful idea received increasing credence in the early 1980s as the dangers of HIV transmission by blood transfusions become apparent. As a consequence, blood screening technology has become increasingly sophisticated and the chances of exposure to HIV from a blood transfusion dropped from 1 in 5,000 in the early 1980s to about 1 in 600,000 today. Nonetheless, there are still a variety of problems and risks with banked blood that are expected to persist in the foreseeable future.

Development of a successful blood substitute would eliminate the need to match blood types when transfusing trauma victims, as well as the risk that HIV, hepatitis or other pathogens could be transmitted by transfusion. The emergence of new viral threats such as SARS and "bird flu" illustrate the ongoing vulnerability of the world-wide blood supply to new and/or under-appreciated diseases for which reliable screening technology may not yet exist. In addition, a ready supply of synthetic blood substitute would also stretch natural blood supplies, which often run short around the holidays. For example, as recently as 2000 almost 10 percent of U.S. hospitals reported that they had to postpone surgeries because of unanticipated blood shortages. Finally, even when safe from contamination, blood transfusions can have negative effects on the immune system of the recipient.

Although blood is responsible for a multitude of functions in the body, a synthetic blood substitute would serve only to replicate its gas transporting function in which fresh oxygen is carried to cells and organs, exchanged there for carbon dioxide, and carbon dioxide is then removed. These are the most immediate and critical functions of blood, particularly in cases where blood is lost through massive trauma.

Two main approaches to such synthetic blood substitutes have been pursued over the past three decades: modified hemoglobin from human, animal, or recombinant origin and fluorocarbon emulsions. The hemoglobin approach is appealing because it most directly mimics the mechanism of oxygen transport in natural blood. However, when hemoglobin is not contained within a red blood cell, it is actually toxic to humans and most animals. Hence, much research on artificial hemoglobin focuses on reducing its toxicity through genetic engineering, chemical crosslinking, or attaching synthetic protective coatings that mimic the function of red blood cells. Although these approaches can ameliorate the issue of acute toxicity, hemoglobin-based blood substitutes also scavenge nitric oxide, leading to unwanted vasoconstriction and, hence, increased systemic and pulmonary artery pressure.

In the fluorocarbon approach, attempts to closely mimic natural blood are abandoned in favor of a purely synthetic mode of oxygen transport. In living systems, hemoglobin delivers oxygen in response to the cofactor 2,3-diphosphoglycerate (2,3-DPG). In contrast, the mechanism for oxygen delivery and carbon dioxide removal with fluorocarbons is simply a response to differences in the partial pressures of these gasses.

Attractive forces between fluorocarbon molecules are known to be particularly weak, and because of this, gas molecules are able to occupy molecular cavities between them, leading to the observed high gas solubilities. In general, gas solubilities in fluorocarbons follow the order of $He < H_2 < N_2 < CO < O_2 << CO_2$, where gases with the largest molecular volumes possess the highest solubilities. Fluorocarbons are also generally highly inert and nontoxic.

Because fluorocarbons are very hydrophobic, they tend to have desirably short residence times in various organs of the body. However, their extreme hydrophobicity is also a problem because blood plasma is an aqueous system that does not dissolve hydrophobic solutes. This problem has been addressed for many years through encapsulation of liquid fluorocarbons in a variety of sophisticated emulsion systems, which help to keep liquid fluorocarbons dispersed in aqueous media like blood plasma for, in some cases, very long periods of time. This is accomplished through use of sophisticated mixed fluorocarbon-hydrocarbon surfactants. Biocompatibility of these is optimized through judicious choice of the hydrophilic "head-group." Particle sizes in the best emulsions can be as small as 0.1 μm. Nevertheless, choosing the right fluorocarbon and emulsion formulation is a fine art that balances concerns about oxygen solubility, fluorocarbon volatility, emulsion size, emulsion stability and residence time in various organs of the body. Hence, the vast majority of research and development activities on fluorocarbon-based blood substitutes has focused on engineering improved surfactants and emulsion formulations.

Fluorocarbon emulsions are removed from the blood stream and eventually expelled from the body primarily in two major steps. In the first step, the fluorocarbons are taken up and stored in reticuloendothelial system (RES) organs such as the liver, spleen and bone marrow. The rate of uptake in this step is strongly dependent on emulsion stability, droplet size, and hence, choice of emulsifying agent (surfactant). As an example, it was found that one particular egg yolk phospholipid (EYP)-coated fluorocarbon emulsion had an intravascular half-life ($t_{1/2}$) in rats of 14 hours for a 2.7 g/kg dose with average droplet diameter of 0.09 μm. Surface modification using other surfactants than EYP led to shorter $t_{1/2}$.

In the second step, which is much slower than the first, the fluorocarbons are released from the RES back into circulation, where they are taken up by circulating lipid carriers (lipoproteins and chylomicrons) and moved to the lungs for excretion through the lung alveoli into expired air. The excretion rate of the latter step strongly depends on the fluorocarbon molecular weight and lipophilicity.

Accordingly, there is a need for improved synthetic oxygen carriers for biomedical and biotechnical applications, which exhibit reduced toxicity, improved temperature stability, improved shelf life, and which overcome the various problems associated with the development of stable microemulsions.

SUMMARY OF THE INVENTION

The invention offers desirable combinations of properties for oxygen carriers capable of functioning as synthetic blood substitutes for various biomedical and biotechnical applications, including resuscitation of trauma victims that have suffered massive hemorrhaging, and transfusions for human and veterinary surgical procedures. Other applications for the oxygen carrier compounds of the invention include incorporation of the compounds in solutions containing contrast agents used in ultrasonic in vivo imaging, and as bioreactor additives for use in commercial cell culture applications. The compounds of this invention have advantages over whole blood and blood derivatives, fluorocarbon blood substitutes, and modified hemoglobin blood substitutes. These advantages include improved long-term storage stability, and temperature stability. A further advantage with respect to whole blood and blood derivatives is that the oxygen carrying compounds of the invention may be used for cardiopulmonary resuscitation and transfusion without regard to the blood type of the patient. An expected further advantage of the oxygen carrying compounds of the invention with respect to conventional synthetically modified hemoglobin blood substitutes is reduced physiological side effects. Specifically, the compounds of the invention are not expected to scavenge nitric oxide, and are not expected to cause undesirable vasoconstriction, and increased systemic and pulmonary artery pressure. A further advantage of the oxygen carrying compounds of the invention with respect to conventional fluorocarbon synthetic blood substitutes is that the synthetic oxygen carrying compounds of the invention can be synthesized to present exterior functional groups that are highly soluble in aqueous blood plasma, thereby eliminating the need for overcoming problems associated with development of stable fluorocarbon emulsion formulations.

The various advantages of the invention are achieved by providing a nano-structured blood substitute that comprises a fluorocarbon-containing dendritic polymer or a fluorocarbon-modified dendritic polymer compound having a dendritic polymer core and fluorocarbon spacers covalently bonded to the dendritic polymer core, and hydrophilic moieties covalently bonded to terminal groups of the fluorocarbon-containing dendritic polymer or to the fluorocarbon spacers of the fluorocarbon-modified dendritic polymer.

The various advantages of the invention are achieved in accordance with another aspect of the invention by providing a dendritic polymer comprised of fluorocarbon repeat units, and having hydrophobic moieties covalently bonded to the fluorocarbon spacers.

These and other features, advantages and objects of the present invention will be further understood and appreciated by those skilled in the art by reference to the following specification, claims and appended drawings.

DESCRIPTION OF THE PREFERRED EMBODIMENTS

The oxygen carrying compounds of this invention are nano-structured materials having interior fluorocarbon segments or moieties that are capable of accommodating large volumes of oxygen or other dissolved gasses, and which have exterior segments or moieties that render the entire molecule highly soluble in aqueous media, such as blood plasma. The expression "nano-structured" refers to the fact that the oxygen carrying compounds of this invention are nanoscopic (typically having a size from about 1 nm to about 15 nm) and are highly structured in the sense that chemically different segments or domains within each molecule are spatially arranged with respect to each other in a specific predetermined manner to perform specific cooperative functions. In particular, the oxygen carrying molecules of the invention are structured to have a hydrophobic interior capable of carrying oxygen and/or other gasses, and a hydrophilic exterior that renders the entire molecule soluble in aqueous medium. The molecular architecture creates flexible pockets beneath the surface of the hydrophilic exterior that can expand to accommodate potentially large volumes of oxygen or other dissolved gasses.

Figure 4:
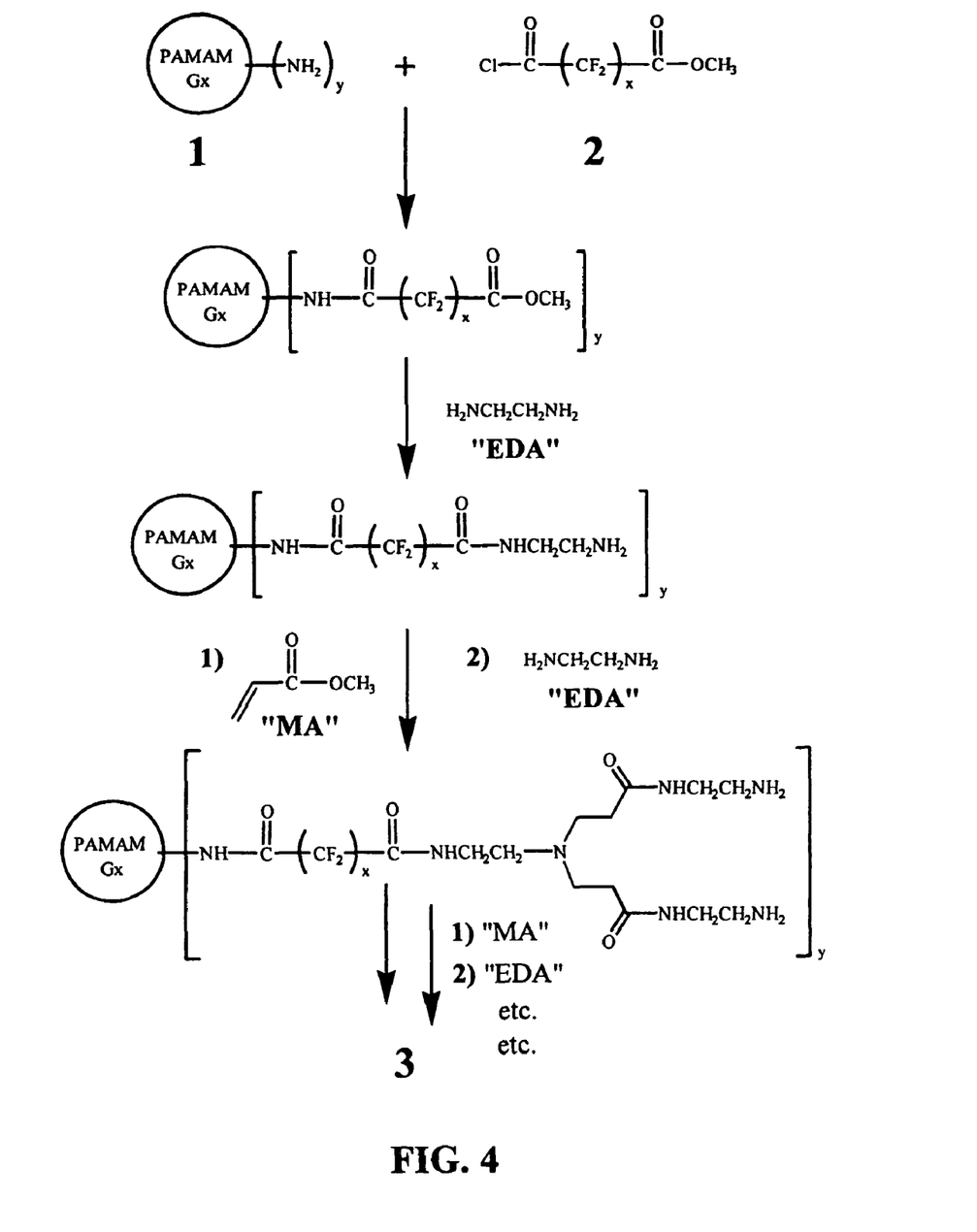
FIG. 4 is a reaction scheme illustrating the overall strategy of the synthesis of a dendritic polymer compound in accordance with an aspect of this invention, which is capable of carrying oxygen.
Figure 5:
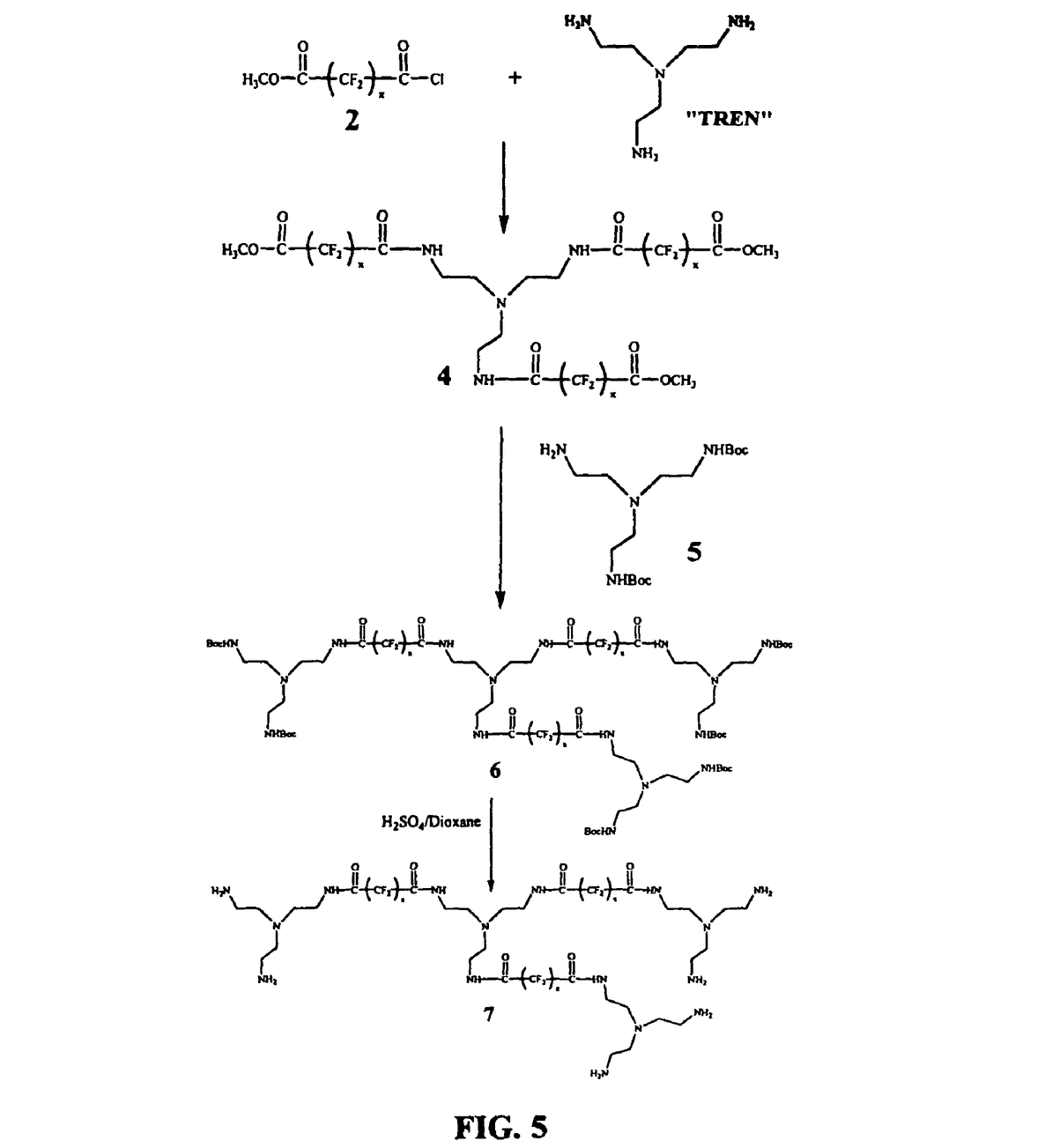
FIG. 5 is a reaction scheme illustrating a synthetic strategy for preparation of multi-layered perfluorinated dendrimers.
Figure 6:
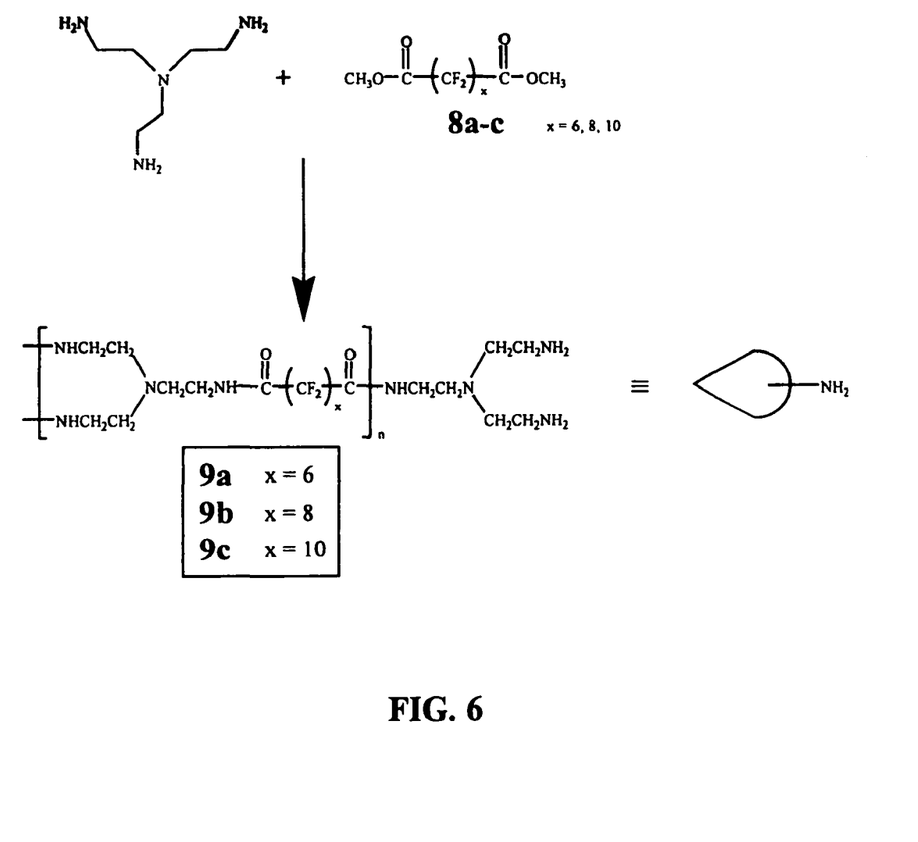
FIG. 6 is a reaction scheme illustrating a synthesis of hyperbranched perfluoro polyamides.
Figure 10:
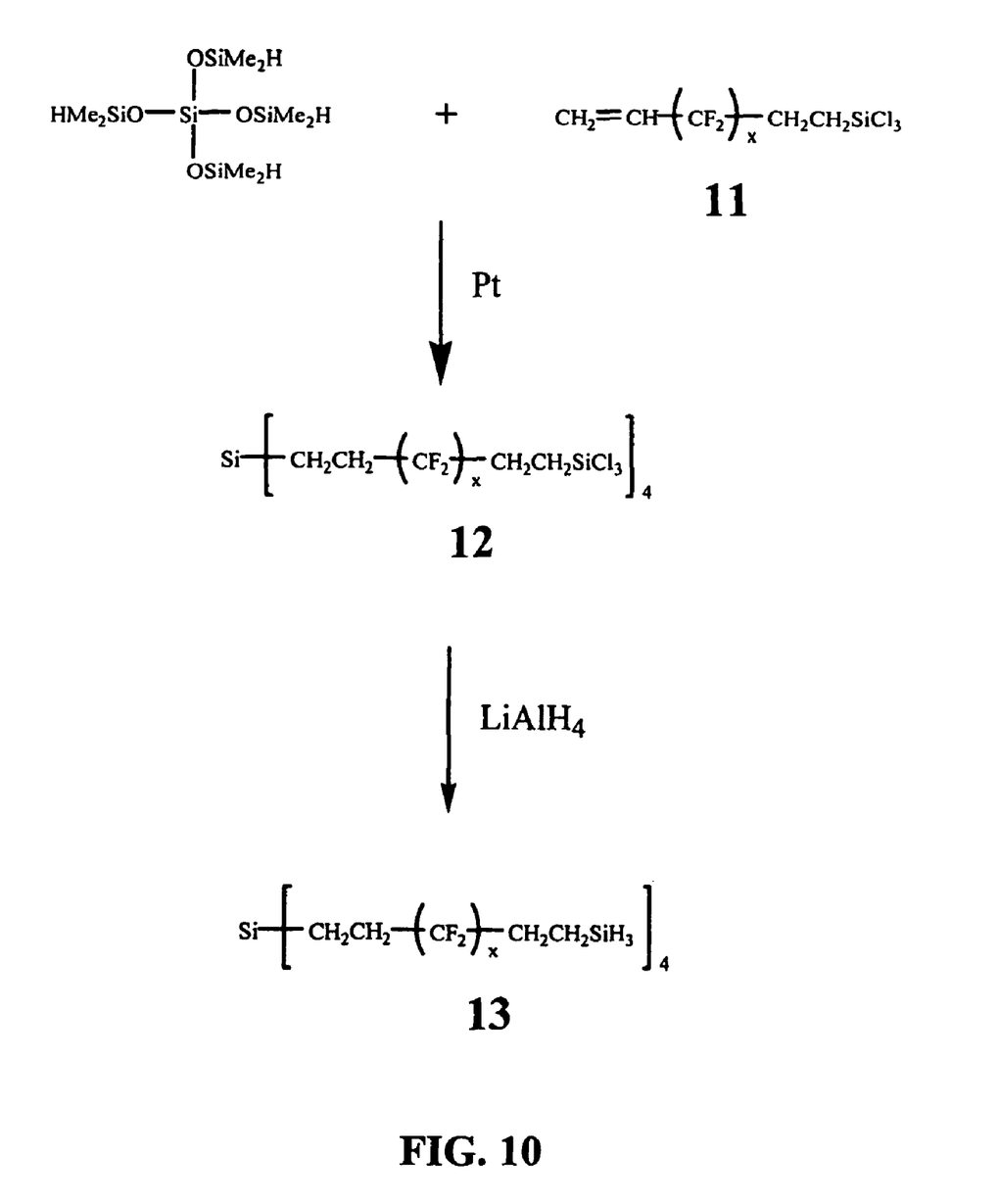
FIG. 10 is a reaction scheme illustrating a synthetic strategy for preparation of multi-layered perfluorinated organosilicon dendrimers.
Figure 11:
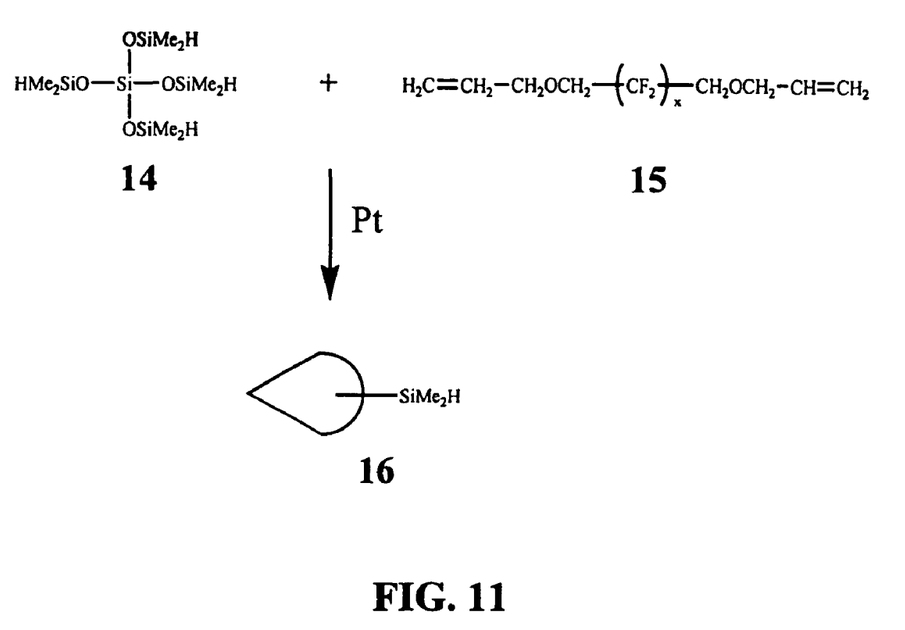
FIG. 11 is a reaction scheme illustrating a synthesis of hyperbranched perfluoro carbosiloxanes.

Because they are synthesized in a highly controlled, stepwise manner, and are purified between each synthetic step, the dendrimer compositions shown in FIGS. 4, 5 and 10 are expected to have the most precise spatially resolved structures, as well as nearly monodisperse shapes, sizes, and molecular weights. These would be most appropriate for in vivo applications such as blood substitutes and ultrasonic contrast agents. The hyperbranched polymers in FIGS. 6 and 11 are expected to be less structurally precise and monodisperse than the dendrimers. However, these will still possess a significant degree of nanoscaled structural precision (radially segregated nanodomains) due to their hydrophobic, highly fluorinated interiors and hydrophilic peripheries. The structure and higher polydispersities of hyperbranched polymers makes them more appropriate for in vitro applications, such as cell culture additives.

The nano-structured dendrimers of the invention offer desirable combinations of properties for synthetic blood substitutes because of their unique characteristics. These characteristics include very well-defined nanoscopic molecular sizes that can be precisely selected to within about 1 nm; discrete and reproducible globular shapes, controllable through precise synthetic design; inherent flexibility and chemical stability as single macromolecules; low cytotoxicity; and hydrophilicity of the exterior that provides compatibility with blood plasma. The nanoscopic size and globular shape of these materials (e.g., <15 nm) produce significantly enhanced solubility over high molecular weight linear polymers of similar chemical composition. In addition to this, efficient excretion through the kidneys is highly dependent on the right combination of size and hydrophilicity. The therapeutic macromolecules of this invention will easily pass through the kidneys due to the enhanced permeability of nanoscaled objects through the kidney membranes, as well as reduced affinity towards them. This achievement of precise control over size, shape and solubility at the nanoscopic size range is a major step forward in the field of synthetic blood substitutes.

The dendritic core may be viewed as the architectural foundation upon which the nano-structured oxygen carrying compound is built. This analogy helps illustrate the fact that the chemical composition and properties of the dendritic core are not particularly critical. Nevertheless, it is desirable that the dendritic core provides a spherical or globular foundation, is relatively stable and inert under the conditions in which the oxygen carrying compounds are used and stored, and has a high density of exterior functional groups upon which the highly fluorinated region of the molecule (which accommodates oxygen and/or other small molecules) is assembled. Thus, generally any dendritic polymer meeting these criteria would be suitable for use as the core for the oxygen carrying compounds. Because of their commercial availability, biocompatibility and low toxicity, polyamidoamine (PAMAM) dendrimers, $[-CH_2CH_2C(O)NHCH_2CH_2N=]_m$, are an example of a preferred dendritic core for use in the invention.

Figure 1:
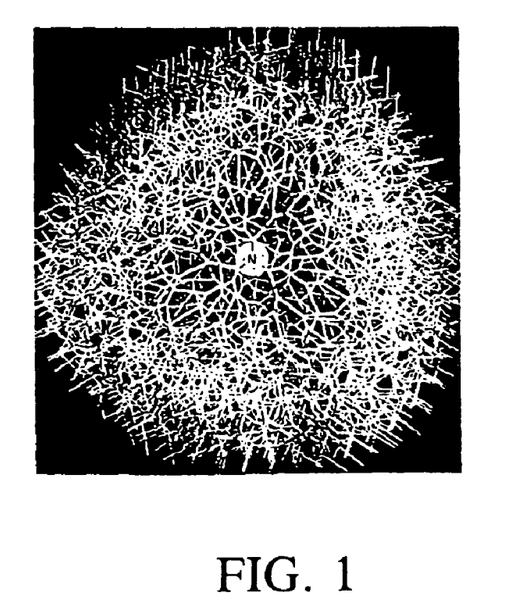
FIG. 1 is a schematic representation of the dense-shell molecular architecture of a dendrimer.
Figure 2:
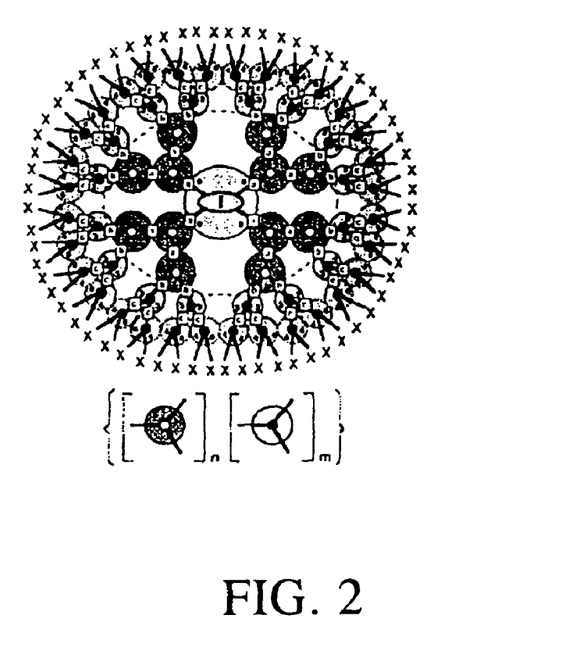
FIG. 2 is a representation of a dendrimer molecule, which shows its radially-layered branch cell organization.

Dendrimers are globular macromolecules which consist of two or more tree-like dendrons, emanating from either a single central atom or an atomic group, called the core (N in FIG. 1). The main building blocks of dendrimer architecture are the branch cells (large circles in FIG. 2), which represent dendritic repeat units and always contain at least one branch juncture (small circles in FIG. 2). In an idealized case of complete and perfect connectivity (i.e., in an ideal dendrimer), these branch cells are organized in a series of regular, radially concentric layers (called generations) around the core. Each of these layers contains a mathematically precise number of branch cells that increases in a geometrically progressive manner from the core to the outer dendrimer surface.

Dendrimers are synthesized by adding repetitive branch units to the molecule one layer or generation at a time in iterative growth steps. With rigorous process control and purification methods after each iterative growth cycle, they can be synthesized with very high degrees of purity and extremely narrow polydispersities. Dendrimer size increases with generation number, leading to crowding of the surface functional groups, which causes the dendrimer to adopt a spherical or globular shape at a sufficiently high generation. Interaction with other molecules in solution or vapor phase can occur through both exo- and endoreception. Exoreception occurs when molecular species interact with functional groups at the termini of each dendrimer arm. These interactions are facilitated by the relatively easy accessibility of the exo-presented end-groups (X of FIG. 2), which are available in very high molecular density as a consequence of the dendritic molecular architecture. Endoreception occurs when species penetrate the interstices between the (potentially) densely packed surface groups and are solvated or otherwise occluded within the dendrimer interior.

Figure 3:
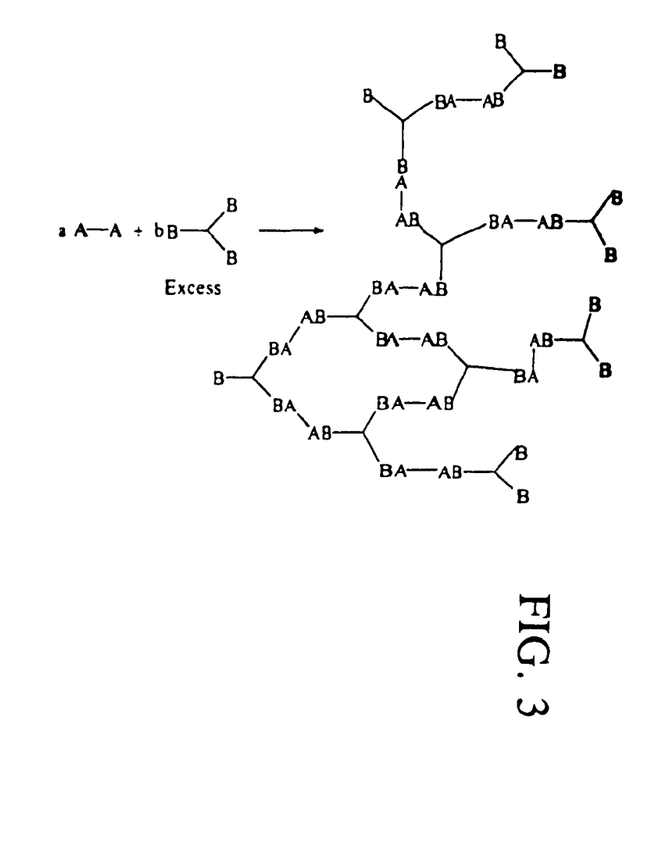
FIG. 3 is a schematic representation of the synthesis of hyperbranched polymers with either of two possible end-groups by a bi-molecular polymerization reaction involving either excess of $A_2$ or excess of $B_3$ type monomers.

Similar to dendrimers, hyperbranched polymers, such as those schematically represented in FIG. 3, are also tree-like macromolecules that possess extensive branching. However, in contrast to dendrimers, they are less regular, have statistically random size and shape distributions, and are significantly more economical and easier to prepare by various one-step, one-pot procedures, instead of multi-step iterative processes required for dendrimers. As a consequence, hyperbranched polymers have attracted considerable attention as potential substitutes for more expensive dendrimers. Although their lesser degree of structural perfection makes them less suitable for some biomedical applications such as oral or intravenous drug delivery, they are very well suited for other uses such as topical drug delivery, some biotechnical reactor-based processes and the construction of solid-state biomimetic materials.

Hyperbranched polymers are traditionally prepared by mono-molecular polymerization reactions of $AB_2$, $AB_3$ or in general $AB_x$ monomers, where x is an integer larger than unity. The less common approach is Michigan Molecular Institutes' patented bi-molecular polymerization of $A_2+B_3$, $A_2+B_4$, or in general an $A_2+B_y$ monomer system where x and y are integers and the ratio of A to B groups (r=A/B) is controlled between the theoretical values ranging within $1/[(x-1)(y-1)]>r>(x-1)(y-1)$ in order to avoid gelation. The latter approach has several important advantages over the former: (a) there is a significantly larger variety of different $A_x$ and $B_y$ monomers commercially available, (b) the A/B ratio of the reacting functionalities can be adjusted at will to control the mass of the resulting hyperbranched molecules, and (c) both A and B units can become terminal end-groups, depending on which one of x or y is greater. To illustrate this versatility, two extreme cases of hyperbranched polymers prepared from an $A_2+B_3$ system are shown in FIG. 3.

Hyperbranched polymers may be viewed as intermediate between randomly branched polymers and dendrimers. More specifically, a hyperbranched polymer contains a mixture of linear and fully branched repeating units, whereas an ideal dendrimer contains only fully branched repeating units, without any linear repeating units. The degree of branching, which reflects the fraction of branching sites relative to a perfectly branching system (i.e., an ideal dendrimer), for a hyperbranched polymer is greater than zero and less than 1, with typical values being from about 25% to 45%. Unlike ideal dendrimers which have a polydispersity of 1, hyperbranched polymers have a polydispersity that typically increases with increasing molecular weight, with typical polydispersities being greater than 1.1 even at relatively low molecular weight such as 1,000 Daltons, and with polydispersities greater than 1.5 being common for hyperbranched polymers having a molecular weight of about 10,000 or higher. These differences between the polydispersities and degree of branching of hyperbranched polymers as compared with dendrimers is indicative of the relatively higher non-ideality, randomness, and irregularity of hyperbranched polymers as compared with dendrimers, and distinguishes hyperbranched polymers from dendrimers.

The fluorocarbon spacers can be covalently bonded to the terminals of the dendritic core using any of a variety of well-known chemistries. For example, a carboxylic acid terminated fluorocarbon spacer can be covalently bonded to an amine-($NH_2$) terminated dendritic polymer via an amidation reaction. Various other well-known addition reactions may also be employed. The fluorocarbon linker is generally a linear or lightly branched residue of a di- or poly-functional molecule having a plurality of fluorocarbon (—$CF_2$—) units. Preferred fluorocarbon linkers are generally the residues of bi-functional linear fluorocarbons having segments with the chemical formula —$(CF_2)_x$—, wherein x is an integer greater than 1, typically from about 6 to about 12.

After the fluorocarbon spacers have been covalently bonded with the dendritic polymer core, reactive terminal functional groups at the free end of the fluorocarbon spacers are used for attachment of hydrophilic moieties. Suitable hydrophilic moieties include dendrons or focal point monofunctional hyperbranched polymers prepared via traditional polymerization reactions of $AB_x$ monomers. Hydrophilic dendrons may be covalently bonded to terminal functional groups of the fluorocarbon spacers by sequential addition of branch units one layer or generation at a time in an iterative growth process similar to that used for forming dendrimers. As with dendrimers, rigorous process control and purification after each iterative growth cycle facilitates synthesis of very high purity compounds having an extremely narrow polydispersity, such that the dendrons attached to each of the fluorocarbon spacers are identical. For example, when the reactive functional group at the free terminal of the fluorocarbon spacer bonded to the dendritic polymer core is an amine (—$NH_2$), sequential addition of methyl acrylate and ethylene diamine may be utilized to provide PAMAM dendrons at the exterior of the oxygen carrying compound. Typically, two to four iterations of the two reaction steps will provide desirable solubility of the compound in an aqueous solution. As another alternative, individual dendrons or focal point monofunctionalized hyperbranched polymers may be separately synthesized and subsequently covalently bonded to the free terminals of the dendritic core-bound fluorocarbon spacers.

In order to improve biocompatibility and reduce toxicity, particularly for in vivo applications, the oxygen carrying compounds of the invention comprising a dendritic polymer core, fluorocarbon spacers covalently bonded to the dendritic core, and hydrophilic terminal moieties covalently bonded to the fluorocarbon spacers, may be further modified. Dendrimers with primary amine end-groups are hemolytic and cytotoxic at relatively low concentrations, and have undesirably low circulation times. Accordingly, it may be desirable to further modify oxygen carrying compounds having PAMAM terminal dendrons to improve biocompatibility and circulation times, and to reduce toxicity. Several bioconjugation strategies may be employed for achieving improved biocompatibility and reduced toxicity. Modifications which achieve improved biocompatibility, higher circulation times, and reduced toxicity include acetamidation or bioconjugation with sugars, polyols, phosphoramidates, phosphocholines and glycerophosphocholines. Specific examples include glycidol, D-glucono-δ-lactone, xylitol, maltose, sucrose and trehalose functional groups. In general, biocompatibility modifications involve reacting cytotoxic, hemolytic, or otherwise undesirable exposed functional groups to provide highly biocompatible hydroxylated surfaces.

The oxygen carrying compounds of this invention may be beneficially employed in various biomedical and biotechnical procedures including pulmonary resuscitation, transfusion, perfusion, additives for bioreactors, etc. The expression "oxygen carrying compound" as used herein refers to compounds that are capable of occluding and releasing oxygen or other low molecular weight gas molecules. The oxygen carrying compounds may be stored in a dry state, reconstituted and loaded with oxygen by being contacted with an aqueous medium containing a high level of dissolved oxygen for a period time necessary to achieve a desired oxygen loading. Such materials in dry form may be stored for long periods of time at relatively high or relatively low temperatures in a dry and sterile condition without any deterioration. Alternatively, the oxygen carrying compounds of this invention may be stored in the form of a highly concentrated solution (e.g., dissolved in an artificial plasma solution) which is suitable for use in transfusions, cardiopulmonary resuscitation, etc. It is anticipated that solutions of this type may contain high levels of the oxygen carrying compound (e.g., 50 to 75% by weight, or higher), and thereby facilitate rapid delivery of oxygen utilizing relatively small quantities of solution. The compounds and compositions of this invention may be utilized to great benefit to reduce battlefield and catastrophic disaster mortality and morbidity.

In an alternative embodiment of the invention, the oxygen carrying dendritic polymer compounds containing highly fluorinated interior segments and having exterior segments that render the entire molecule highly soluble in aqueous media, such as blood plasma, comprise a dendritic polymer having fluorocarbon segments, and hydrophilic terminal groups. In accordance with this aspect of the invention, rather than having a dendritic polymer core and fluorocarbon spacers covalently bonded to the dendritic core, the fluorocarbon moieties are incorporated into the monomers used for preparing the dendritic polymer. As with the above described oxygen carrying molecules comprising a dendritic core, fluorocarbon spacers and hydrophilic exterior moieties, the dendritic fluorocarbon polymers (typically either dendrimers or hyperbranched polymers) are provided with hydrophilic exterior moieties (e.g., functional groups or dendrons, such as polyamidoamine dendrons), and may be further reacted or conjugated with various materials that improve biocompatibility and reduce cytotoxicity (e.g., bioconjugation with sugars, polyols, phosphoramidates, phosphocholines and glycerophosphocholines). Also, as with the tri-segmented materials described above, the materials in accordance with this aspect of the invention may be stored in either a dry condition or in a concentrated solution, and exhibit excellent long-term storage stability at both low and high temperatures.

Further understanding of the invention will be facilitated by consideration of the following examples which are intended to illustrate certain embodiments of the invention.

Example 1

The overall strategy of the synthesis of a dendritic polymer compound capable of carrying oxygen is schematically illustrated in FIG. 4. In the first step, an amine terminated PAMAM dendrimer is reacted with a perfluorinated acid chloride-methyl ester, which may be prepared though monohydrolysis of perfluorinated dimethyl ester, followed by conversion to acid chloride. The acid chloride functional group will attach preferentially to the amine end-groups of the PAMAM dendrimer due to its higher reactivity. The strategy for attaching hydrophilic dendritic branches to the omega ends of the fluorocarbon spacer arms is also illustrated in FIG. 4. Additional generations of PAMAM dendrons may be grown divergently from the surface of the modified dendrimer by repeating the last two steps shown in FIG. 4 (addition of methyl acrylate and ethylene diamine) as many times as desired. Repetition of these two steps is expected to allow complete water solubility of the resulting compound.

Example 2

FIG. 5 illustrates a strategy for the synthesis of multi-layer perfluorinated dendrimers, which is based on acid chloride-methyl ester and di-protected triamine. The first step involves coupling of three equivalents of acid chloride methyl ester with a triamine. This is followed by reaction of the obtained product with three equivalents of di-protected triamine. Because it contains two protected groups, stoichiometric amounts of the di-protected triamine will be sufficient. The final step involves removal of the BOC protecting groups, which can be achieved using well-known synthetic polypeptide chemistries, such as treatment with trifluoroacetic acid or sulfuric acid in dioxane. Subsequent generations of branches may be grown through sequential addition of acid chloride-methyl ester and di-protected triamine, followed by removal of the protecting groups. The resulting multi-layered perfluorinated dendrimer may be utilized as an oxygen carrier for various applications without further modification, or may be further modified to improve biocompatibility and reduced toxicity for in vivo use.

Example 3

FIG. 6 schematically illustrates synthesis of hyperbranched perfluoro polyamide. Perfluoro dimethyl ester may be polymerized with triamine in a one-step, one-pot reaction, without use of protecting groups. Formation of a crosslinked network may be avoided through careful adjustment of stoichiometry, as discussed above. The resulting hyperbranched perfluoro polyamide may be used as an oxygen carrier in biomedical and/or biotechnical applications.

A 250 mL round bottom flask was charged with tris(2-aminoethyl)amine (TREN) (13.0 g, 0.0888 mol) and anhydrous MeOH (100 mL). The flask was flushed with $N_2$ for 3 minutes. The solution was cooled to $-20°$ C., followed by dropwise addition of a solution of dimethyl hexadecafluorosebacate (34.56 g, 0.0666 mol) dissolved in 120 mL anhydrous methanol and 30 mL anhydrous THF into the mechanically stirred reaction mixture. After stirring for 2 hours at $-20°$ C., the reaction mixture was allowed to warm to room temperature, and was stirred for an additional 16 hours. Volatile solvents were removed by rotary evaporation, yielding a sticky solid. This was redissolved in MeOH and subjected to ultrafiltration using a 1000 MWCO cellulose membrane. Ultrafiltration was halted when 50 mL of liquid remained in the chamber, and the contents were transferred in a pear-shaped flask. The solvent was removed by rotary evaporation, once again yielding a sticky solid, and this was further dried under high vacuum for 16 hours. A light yellow solid (38.0 g) designated as HB—$(CF_2)_8$—$(NH_2)_x$ was obtained. $^1$H NMR in $CD_3OD$: 3.30-3.42 ppm [m, —CONHC$\underline{H}_2$—CH$_2$—N=]; 2.54-2.78 ppm [m, —CONHCH$_2$—C$\underline{H}_2$—N=]. $^{13}$C NMR in $CD_3OD$: 159.56 ppm [—C=O]; 106.0-116.47 ppm [m, —(C$\underline{F}_2$)$_8$]; 57.38 ppm [—CH$_2$—]; 54.33 ppm [—CH$_2$—]; 40.09 ppm [—CH$_2$—]; 39.33[—CH$_2$—]. $^{19}$F NMR in $CD_3OD$: -120.90 ppm (s, —C$\underline{F}_2$—CO—); -122.92 ppm (s, —C$\underline{F}_2$—CF$_2$—CO—); -123.17 ppm (s, —C$\underline{F}_2$—CF$_2$—CF$_2$—CO—); -123.91 ppm (s, —C$\underline{F}_2$—CF$_2$—CF$_2$—CF$_2$—CO—). IR on KBr pellet (selected peaks in cm$^{-1}$): 2948, 2807, 1701, 1553, 1453, 1353, 1036, 947. MALDI-TOF (matrix: 2,5-Dihydroxybenzoic acid): 16 apparent groups (770.3 m/z, 1367.7 m/z, 1960.0 m/z, 2558.4 m/z, 3149.8 m/z, 3710.0 m/z, 4301.2 m/z, 4886.3 m/z, 5476.6 m/z, 6072.5 m/z, 6658.3 m/z, 7250.1 m/z, 7840.9 m/z, 8428.0 m/z, 9025.0 m/z, 9612.1 m/z) within the total range from 700 to 10000 m/z together with some weak groups at two ends of the range. TGA (20° C./min., air): onset of mass loss at 140° C., 50% mass loss at 375° C., 100% mass loss at 675° C. DSC (10° C./min., nitrogen): 19.45° C. ($T_g$).

Example 4

Figure 7:
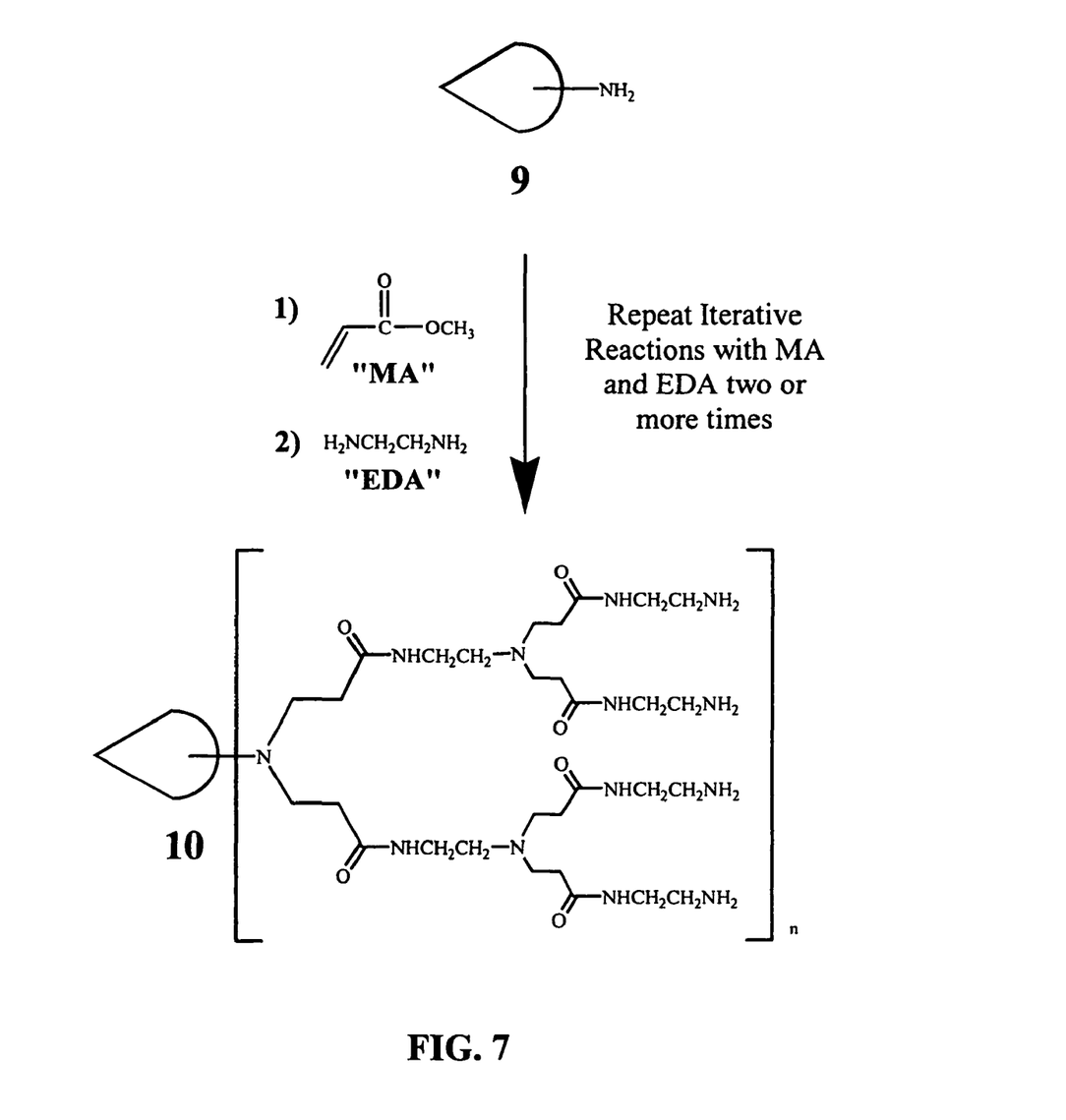
FIG. 7 is a reaction scheme illustrating a synthetic strategy for divergent growth of polyamidoamine branches from the periphery of perfluorinated polyamide dendrimers and hyperbranched polymers.

Improved water solubility of the dendritic polymer from Example 2, or the hyperbranched perfluoro polyamide from Example 3 may be accomplished through divergent growth of PAMAM dendrons from their periphery, as shown in FIGS. 4 and 7. Addition of methyl acrylate and ethylene diamine is repeated as many times as desired. In practice, divergent growth of two generations from the periphery of the hyperbranched perfluoro polyamide from Example 3 yielded polymers that had nearly 50 weight % solubility in water.

A 250 mL round bottom flask was charged with hyperbranched perfluoroamide [HB—$(CH_2)_8$—$(NH_2)_x$, 9 in FIG. 7] (4.0 g 6.0 mmol) and MeOH (50 mL). The reaction mixture was magnetically stirred until the hyperbranched polymer fully dissolved, and methyl acrylate (4.18 g, 48.0 mmol) was added to the flask. The reaction flask was covered and the solution was stirred at room temperature for 72 hours. After completion of reaction, the product was concentrated by rotary evaporation. A small amount of toluene was added and the resulting mixture was purified by ultrafiltration through a 1000 MWCO membrane using MeOH as the eluting solvent. Vacuum drying of the purified product yielded a viscous brown solid, designated as HB—$(CH_2)_8$—$(NH_2)_x$-G0.5 (6 g). $^1$H NMR in $CD_3OD$: 3.65 [s, C$\underline{H}_3$O—C=O]; 3.30-3.44 ppm [m, —CONHC$\underline{H}_2$—CH$_2$—N=]; 2.44-2.84 ppm [m, —CONHCH$_2$—C$\underline{H}_2$—N=]. $^{13}$C NMR in $CD_3OD$: 175.05 ppm [CH$_3$O—$\underline{C}$=O]; 159.56 ppm [—C=O]; 106.0-116.47 ppm [m, —(CF$_2$)$_8$]; 57.38 ppm [—CH$_2$]; 54.33 ppm [—CH$_2$]; 40.09 ppm [—CH$_2$]; 39.33 ppm [—CH$_2$]. $^{19}$F NMR in $CD_3OD$: 120.96 ppm [s, —CF$_2$—C=O]; 122.88 ppm [s, —C$\underline{F}_2$—CF$_2$—C=O]; 123.15 ppm [s, —C$\underline{F}_2$—CF$_2$—CF$_2$—C=O]; 123.86 ppm [s, —C$\underline{F}_2$—CF$_2$—CF$_2$—CF$_2$—C=O]. IR, neat film (selected peaks in cm$^{-1}$): 3336, 2956, 2830, 1720, 1544, 1457, 1439, 1359, 1214, 1045, 845. MALDI-TOF (matrix: 2,5-Dihydroxybenzoic acid): 9 apparent groups (1557.4 m/z, 2428.3 m/z, 3293.9 m/z, 4163.2 m/z, 4890.0 m/z, 4886.3 m/z, 5757.9 m/z, 6072.5 m/z, 6628.8 m/z) within the total range from 700 to 10000 m/z together with some weak groups at two ends of the range.

HB—$(CH_2)_8$—$(NH_2)_x$-G0.5 was reacted with ethylenediamine (EDA) to produce G1.0. A 1-L 2-neck flask was charged with EDA (364 g) and 90 mL MeOH. The flask was equipped with an $N_2$ gas inlet, and placed in a constant temperature bath maintained at 6° C. A solution of HB—$(CH_2)_8$—$(NH_2)_x$-G0.5 (6 g) dissolved in 15 mL MeOH, was transferred to the cooled reaction flask, and the reaction mixture was stirred under $N_2$ at 6° C. for six days. The product was concentrated by rotary evaporation, and purified by ultrafiltration through a 1000 MWCO membrane using MeOH as the eluting solvent. The obtained product solution was concentrated by rotary evaporation and dried under vacuum, then lyophilized. A sticky brown liquid designated as HB—$(CH_2)_8$—$(NH_2)_x$-G1.0 (5 g) was obtained. $^1$H NMR in $CD_3OD$: 3.22-3.42 ppm [m, —CONHC$\underline{H}_2$—CH$_2$—N=]; 2.54-2.82 ppm [m, —CONHCH$_2$—C$\underline{H}_2$—N=]; 2.34-2.42 ppm [t, —CONHCH$_2$—C$\underline{H}_2$—NH$_2$]. $^{13}$C NMR in $CD_3OD$: 175.38 ppm [NH$_2$CH$_2$CH$_2$NH—$\underline{C}$=O]; 159.93 ppm [—C=O]; 106.0-118.0 ppm [m, —(CF$_2$)$_8$]; 54.37 ppm

[—CH$_2$]; 53.69 ppm [—CH$_2$]; 51.54 ppm [—CH$_2$]; 46.30 ppm [—CH$_2$]; 44.90 ppm [—CH$_2$]; 34.87 ppm [—CH$_2$]. $^{19}$F NMR in CD$_3$OD: 120.96 ppm [s, —CF$_2$—C=O]; 122.87 ppm [s, —C$\underline{F}_2$—CF$_2$—C=O]; 123.15 ppm [s, —C$\underline{F}_2$—CF$_2$—CF$_2$—C=O]; 123.86 ppm [s, —C$\underline{F}_2$—CF$_2$—CF$_2$—CF$_2$—C=O]. IR on KBr pellet (selected peaks in cm$^{-1}$): 3284, 2948, 2822, 1706, 1648, 1555, 1483, 1325, 1211, 1153, 954. MALDI-TOF (matrix: 2,5-Dihydroxybenzoic acid): 8 apparent groups (633.0 m/z, 862.7 m/z, 1143.6 m/z, 1682.8 m/z, 2498.5 m/z, 2783.9 m/z, 4137.8 m/z, 4420.6 m/z) within the total range from 700 to 10000 m/z together with some very weak groups at two ends of the range. DSC (10° C./min., nitrogen) −22.17° C. (T$_g$).

A 250 mL round bottom flask was charged with hyperbranched perfluoroamide HB—(CH$_2$)$_8$—(NH$_2$)$_x$-G1.0 (4.0 g) and MeOH (100 mL). The reaction mixture was magnetically stirred until the hyperbranched polymer fully dissolved, and methyl acrylate (35 g, 406 mmol) was added to the flask. The reaction flask was covered and the solution was stirred at room temperature for 72 hours. After completion of reaction, the product was concentrated by rotary evaporation. A small amount of toluene was added and the resulting mixture was purified by ultrafiltration through a 1000 MWCO membrane using MeOH as the eluting solvent. Vacuum drying of the purified product yielded a viscous brown solid, designated as HB—(CH$_2$)$_8$—(NH$_2$)$_x$-G1.5 (6 g). $^1$H NMR in CD$_3$OD: 3.67 [s, C$\underline{H}_3$O—C=O]; 3.24-3.44 ppm [m, —CONHC$\underline{H}_2$—CH$_2$—N=]; 2.36-2.84 ppm [m, —CONHCH$_2$—C$\underline{H}_2$—N=]. $^{13}$C NMR in CD$_3$OD: 174.84 ppm [CH$_3$O—$\underline{C}$=O]; 159.44 ppm [—C=O]; 106.50-117.00 ppm [m, —(CF$_2$)$_8$]; 54.92 ppm [—CH$_2$]; 52.30 ppm [—CH$_2$]; 52.28 ppm [—CH$_2$]; 50.66 ppm [—CH$_2$]; 39.32 ppm [—CH$_2$]; 34.64 ppm [—CH$_2$]. $^{19}$F NMR in CD$_3$OD: 120.88 ppm [s, —CF$_2$—C=O]; 122.90 ppm [s, —C$\underline{F}_2$—CF$_2$—C=O]; 123.25 ppm [s, —C$\underline{F}_2$—CF$_2$—CF$_2$—C=O]; 123.85 ppm [s, —C$\underline{F}_2$—CF$_2$—CF$_2$—CF$_2$—C=O]. IR, neat film (selected peaks in cm$^{-1}$): 3335, 2959, 2830, 1721, 1544, 1457, 1439, 1377, 1224, 1049, 855. MALDI-TOF (matrix: 2,5-Dihydroxybenzoic acid): 11 apparent groups (618.9 m/z, 1486.8 m/z, 1893.6 m/z, 2001.0 m/z, 2657.9 m/z, 3058.1 m/z, 3171.0 m/z, 4229.1 m/z, 5397.7 m/z, 6567.7 m/z, 7731.7 m/z) within the total range from 700 to 10000 m/z together with some weak groups at two ends of the range.

HB—(CH$_2$)$_8$—(NH$_2$)$_x$-G1.5 was reacted with ethylenediamine (EDA) to produce G1.0. A 1-L 2-neck flask was charged with EDA (531 g) and 50 mL MeOH. The flask was equipped with an N$_2$ gas inlet, and placed in a constant temperature bath maintained at 6° C. A solution of HB—(CH$_2$)$_8$—(NH$_2$)$_x$-G0.5 (6 g) dissolved in 15 mL MeOH was transferred to the cooled reaction flask, and the reaction mixture was stirred under N$_2$ at 6° C. for six days. The product was concentrated by rotary evaporation, and purified by ultrafiltration through a 1000 MWCO membrane using MeOH as the eluting solvent. The obtained product solution was concentrated by rotary evaporation and dried under vacuum. A sticky brown liquid designated as HB—(CH$_2$)$_8$—(NH$_2$)$_x$-G2.0 (5 g) was obtained (10 in FIG. 7). $^1$H NMR in CD$_3$OD: 3.20-3.42 ppm [m, —CONHC$\underline{H}_2$—CH$_2$—N=]; 2.50-2.84 ppm [m, —CONHCH$_2$—C$\underline{H}_2$—N=]; 2.32-2.42 ppm [t, —CONHCH$_2$—C$\underline{H}_2$—NH$_2$]. $^{13}$C NMR in CD$_3$OD: 175.23 ppm [NH$_2$CH$_2$CH$_2$NH—$\underline{C}$=O]; 159.47 ppm [—C=O]; 107.0-117.0 ppm [m, —(CF$_2$)$_8$]; 54.31 ppm [—CH$_2$]; 53.70 ppm [—CH$_2$]; 51.36 ppm [—CH$_2$]; 46.77 ppm [—CH$_2$]; 45.01 ppm [—CH$_2$]; 43.23 ppm [—CH$_2$]; 42.26 ppm [—CH$_2$]; 35.00 ppm [—CH$_2$]. $^{19}$F NMR in CD$_3$OD: 120.81 ppm [s, —CF$_2$—C=O]; 122.82 ppm [s, —C$\underline{F}_2$—CF$_2$—C=O]; 123.06 ppm [s, —C$\underline{F}_2$—CF$_2$—CF$_2$—C=O]; 123.75 ppm [s, —C$\underline{F}_2$—CF$_2$—CF$_2$—CF$_2$—C=O]. IR on KBr pellet (selected peaks in cm$^{-1}$): 3286, 2947, 2822, 1706, 1645, 1559, 1479, 1326, 1213, 1154, 954. MALDI-TOF (matrix: 2,5-Dihydroxybenzoic acid): 11 apparent groups (1084.7 m/z, 1538.9 m/z, 1761.9 m/z, 2044.8 m/z, 2213.7 m/z, 2579.3 m/z, 2806.5 m/z, 3032.0 m/z, 3314.0 m/z, 4074.1 m/z, 4749.0 m/z) within the total range from 800 to 6000 m/z together with some weak groups at two ends of the range. TGA (10° C./min., air): onset of mass loss at 140° C. 50% mass loss at 305° C., 100% mass loss at 675° C.).

Example 5

Figure 8:
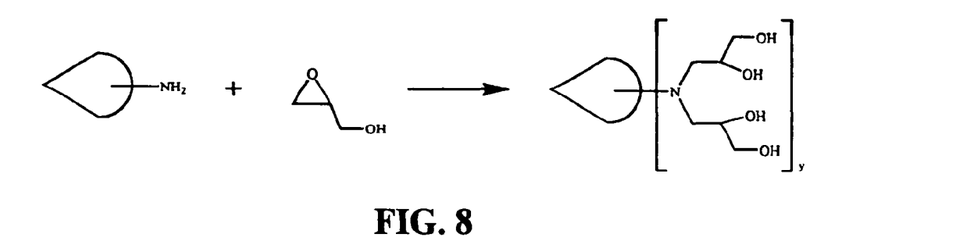
FIG. 8 is a reaction scheme illustrating a synthetic strategy to modify a dendritic polymer with $NH_2$ end-groups to improve its water solubility, improve its biocompatibility, and reduce cytotoxicity.

The dendrimers and hyperbranched polymers from Examples 1-4 may be reacted with glycidol as shown in FIG. 8 to provide a modified compound that exhibits improved solubility in water and other biological fluids, improved biocompatibility and reduced cytotoxicity.

Example 6

Figure 9:
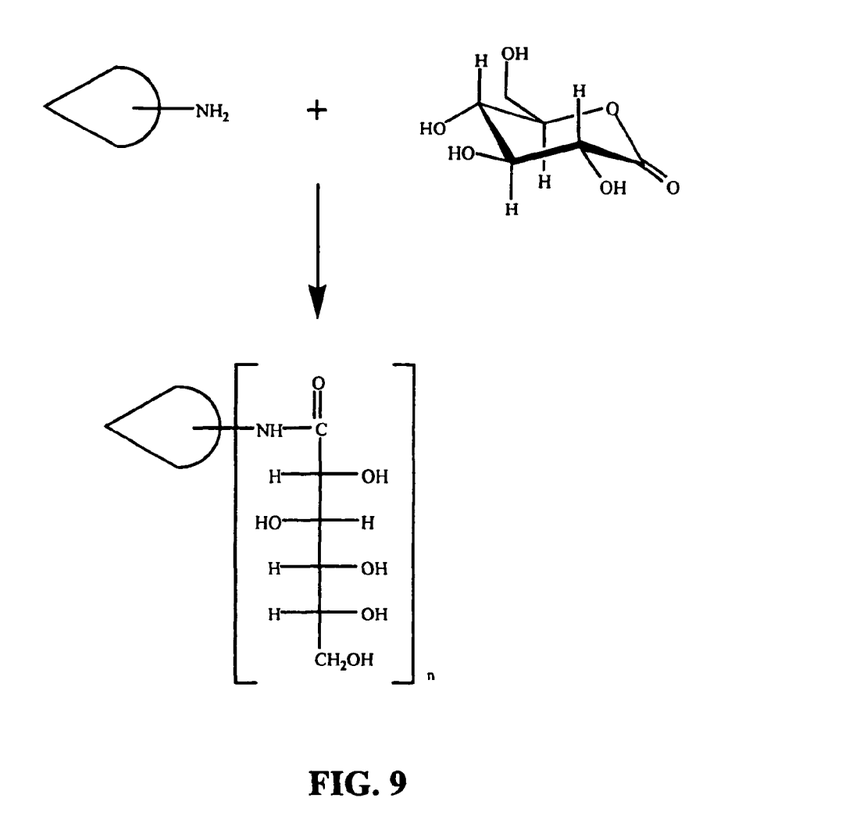
FIG. 9 is a reaction scheme representing a synthetic strategy to bioconjugate an amine terminated dendritic polymer with D-glucono-δ-lactone to improve its biocompatibility and reduce cytotoxicity.

As another alternative, the dendrimers and hyperbranched polymers from Examples 1-4 may be reacted with D-glucono-δ-lactone as shown in FIG. 9 to yield a product that is capable of carrying oxygen and which exhibits improved solubility in water and other biological fluids, improved biocompatibility and reduced cytotoxicity.

A 250 mL round bottom flask was charged with hyperbranched perfluoroamide HB—(CH$_2$)$_8$—(NH$_2$)$_x$-G2.0 (2.0 g), D-glucono-δ-lactone (2.85 g, 16 mmol), and NMP (40 mL). The reaction mixture was heated to 100° C. in a constant temperature bath for 4 hours, with magnetic stirring. Heating was stopped, the reaction mixture was cooled to −10° C., and then stirred for 8 hours while the reaction temperature gradually rose to room temperature. The reaction mixture was diluted to 300 mL with MeOH, and purified by ultrafiltration. The obtained product solution was concentrated by rotary evaporation and dried under vacuum. A sticky brown gum designated as HB—(CH$_2$)$_8$—(NH$_2$)$_x$-G2.0-Glu (9.5 g) was obtained. $^1$H NMR in CD$_3$OD: 4.58 (s, —C—O$\underline{H}$); 3.53 [s, C$\underline{H}_3$O—C=O]; 3.10-3.30 ppm [m, —CONHC$\underline{H}_2$—CH$_2$—N=]; 2.60 ppm [s, —C$\underline{H}_2$OH of gluconolactone]; 2.44-2.84 ppm [m, —CONHCH$_2$—C$\underline{H}_2$—N=]. $^{13}$C NMR in CD$_3$OD: 177.98 ppm [CH$_3$O—$\underline{C}$=O]; 158.69 ppm [—C=O]; 62.68-74.11 ppm [gluconolactone]; 108.0-116.00 ppm [m, —(CF$_2$)$_8$]; 51.30 ppm [—CH$_2$]; 48.97 ppm [—CH$_2$]; 39.42 ppm [—CH$_2$]; 38.60 ppm [—CH$_2$]. $^{19}$F NMR in CD$_3$OD: 120.46 ppm [s, —CF$_2$—C=O]; 122.00-123.05 ppm [b, —C$\underline{F}_2$—CF$_2$—C=O and —C$\underline{F}_2$—CF$_2$—CF$_2$—C=O]; 123.38 ppm [s, —C$\underline{F}_2$—CF$_2$—CF$_2$—CF$_2$—C=O]. IR, neat film (selected peaks in cm$^{-1}$): 3336, 2956, 2830, 1720, 1544, 1457, 1439, 1359, 1214, 1045, 845. MALDI-TOF (matrix: 2,5-Dihydroxybenzoic acid): 9 apparent groups (1080.0 m/z, 1360.5 m/z, 1450.5 m/z, 1590.6 m/z, 1708.8 m/z, 2026.5 m/z, 2209.5 m/z, 2623.4 m/z, 2700.0 m/z, 3021.5 m/z, 3102.0 m/z, 3612.7 m/z) within the total range from 900 to 10000 m/z together with some very weak groups at two ends of the range.

Example 7

FIG. 10. illustrates a strategy for the synthesis of multilayer perfluorinated dendrimers in which organosilicon branching functional groups are used in place of tertiary amine branching units. Dendrimers and hyperbranched polymers with perfluoro organosilicon compositions may have advantages over polyamides and polyamidoamines in terms of improved biocompatibility and reduced cytotoxicity. The first step involves hydrosilylation of tetrakis(dimethylsiloxy) silane with a fluorocarbon that contains an alpha olefin on one end, and a trichlorosilane functional group on the omega end. In the next step the trichlorosilane end-groups are converted to hydridosilane functional groups by treatment with lithium aluminum hydride. Subsequent generations of branches may be grown through hydrosilation with the alpha olefin, omega trichlorosilane repeat unit, followed by treatment with lithium aluminum hydride.

Example 8

FIG. 11 illustrates synthesis of hyperbranched perfluoro polycarbosiloxane. Perfluoro diallyl ether may be hydrosilylated with tetrakis(dimethylsiloxy)silane in a one-step, one-pot reaction. Formation of a crosslinked network may be avoided through careful adjustment of stoichiometry, as discussed above. The resulting hyperbranched perfluoro carbosiloxane may be utilized as an oxygen carrier for various applications without further modification, or may be further modified to improve water solubility and biocompatibility, and to reduce toxicity for in vivo use.

Example 9

Figure 12:
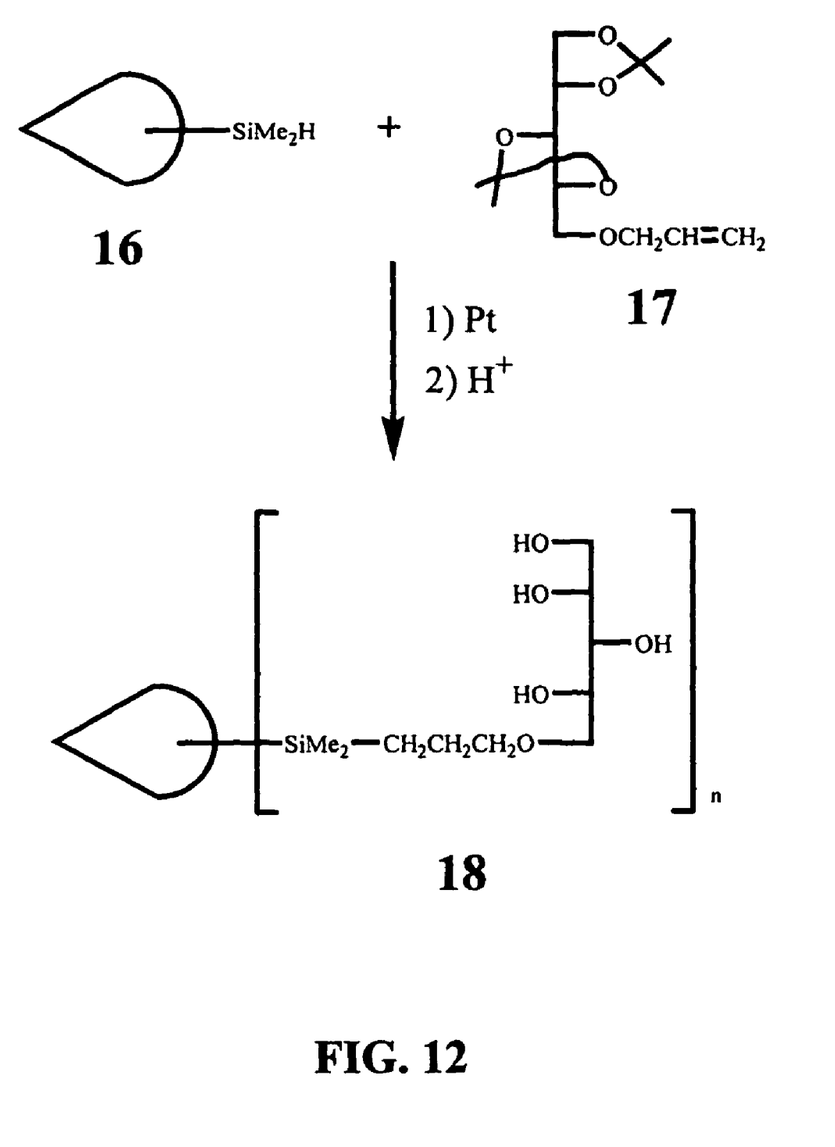
FIG. 12 is a reaction scheme illustrating a synthetic strategy to modify an organosilicon dendrimer or hyperbranched polymer with Si—H end-groups to improve its water solubility, its biocompatibility and reduce cytotoxicity.

The dendrimer from Example 7, or the hyperbranched polymer from Example 8 may be reacted with protected xylitol as shown in FIG. 12 to provide a modified compound that exhibits improved water solubility, improved biocompatibility, and reduced cytotoxicity.

The above description is considered that of the preferred embodiments only. Modifications of the invention will occur to those skilled in the art and to those who make or use the invention. Therefore, it is understood that the embodiments shown in the drawings and described above are merely for illustrative purposes and not intended to limit the scope of the invention, which is defined by the following claims as interpreted according to the principles of patent law, including the doctrine of equivalents.

The invention claimed is:

1. A nano-structured compound capable of carrying oxygen and/or other gases, comprising:
    dendron, dendrimer, hyperbranched polymer, or dendrigraft having a plurality of branches, each branch including a plurality of repeat units that contain a fluorocarbon moiety represented by the formula —$(CF_2)_x$—, wherein x is an integer greater than 1, and each branch including a terminal repeat unit; and
    peripheral hydrophilic moieties covalently bonded to said terminal repeat units to provide solubility of the compound in aqueous media.

2. The nano-structured compound of claim 1, wherein the hydrophilic moieties are dendrons.

3. The nano-structured compound of claim 2, wherein the dendrons are polyamidoamine dendrons.

4. The nano-structured compound of claim 1, wherein the hydrophilic moieties are hyperbranched polymers with a single reactive focal group.

5. The nano-structured compound of claim 4, wherein the hyperbranched polymers with a single reactive focal group are polyamidoamines, polyamides or polyureas.

6. The nano-structured compound of claim 1, wherein the dendron, dendrimer, hyperbranched polymer, or dendrigraft is a dendrimer.

7. The nano-structured compound of claim 1, wherein the dendron, dendrimer, hyperbranched polymer, or dendrigraft is a hyperbranched polymer.

8. The nano-structured compound of claim 1, wherein the dendron, dendrimer, hyperbranched polymer, or dendrigraft is a dendron.

9. The nano-structured compound of claim 1, wherein the dendron, dendrimer, hyperbranched polymer, or dendrigraft is a dendrigraft.

10. The nano-structured compound of claim 1, wherein x is an integer from 6 to 12.

11. The nano-structured compound of claim 1, wherein the compound is bioconjugated with a sugar, polyol, acetamide, phosphoramidate, phosphocholine or glycerophosphocholine.

12. An artificial blood solution comprising:
    an aqueous carrier; and
    a nano-structured dendron, dendrimer, hyperbranched polymer, or dendrigraft that is capable of carrying oxygen and is dissolved in the aqueous carrier, the compound comprising a plurality of branches, each branch having, a plurality of repeat units that contain a fluorocarbon moiety represented by the formula —$(CF_2)_x$—, wherein x is an integer greater than 1, and each branch including a terminal repeat unit; and
    peripheral hydrophilic moieties covalently bonded to said terminal repeat units.

13. The artificial blood solution of claim 12, wherein the hydrophilic moieties are dendrons.

14. The artificial blood solution of claim 13, wherein the dendrons are polyamidoamine dendrons.

15. The artificial blood solution of claim 12, wherein the dendron, dendrimer, hyperbranched polymer, or dendrigraft is a hyperbranched polymer.

16. The artificial blood solution of claim 12, wherein the dendron, dendrimer, hyperbranched polymer, or dendrigraft is bioconjugated with a sugar, polyol, phosphoramidate, phosphocholine or glycerophosphocholine.

* * * * *